United States Patent
Miyamoto et al.

[11] Patent Number: 6,077,408
[45] Date of Patent: Jun. 20, 2000

[54] BIOSENSOR AND METHOD OF MANUFACTURING THE SAME

[75] Inventors: Yoshiko Miyamoto, Suita; Shin Ikeda, Katano; Toshihiko Yoshioka; Shiro Nankai, both of Hirakata, all of Japan

[73] Assignee: Matsushita Electric Industrial Co., Ltd., Osaka-fu, Japan

[21] Appl. No.: 09/002,368

[22] Filed: Jan. 2, 1998

[30] Foreign Application Priority Data

Jan. 31, 1997 [JP] Japan ..................... 9-018733

[51] Int. Cl.⁷ ................................. G01N 27/26
[52] U.S. Cl. ................ 204/403; 204/415; 427/2.11
[58] Field of Search ....................... 204/403, 415, 204/416, 418; 435/817; 427/2.1, 2.11, 2.12, 2.13; 324/450

[56] References Cited

U.S. PATENT DOCUMENTS

| | | | |
|---|---|---|---|
| 4,073,713 | 2/1978 | Newman . | |
| 4,477,575 | 10/1984 | Vogel et al. . | |
| 4,882,013 | 11/1989 | Turner et al. | 205/777.5 |
| 5,421,983 | 6/1995 | Slack et al. | 204/418 |
| 5,512,159 | 4/1996 | Toshihiko et al. . | |
| 5,624,537 | 4/1997 | Turner et al. | 204/403 |
| 5,830,341 | 11/1998 | Gilmartin | 205/777.5 |

FOREIGN PATENT DOCUMENTS

| | | |
|---|---|---|
| 0 136 362 | 4/1985 | European Pat. Off. . |
| 0 359 831 A1 | 3/1990 | European Pat. Off. . |
| 0 470 290 A1 | 2/1992 | European Pat. Off. . |
| 0 513 804 A2 | 11/1992 | European Pat. Off. . |
| 0 593 096 A2 | 4/1994 | European Pat. Off. . |
| 0 636 879 A2 | 2/1995 | European Pat. Off. . |
| 0 685 737 A1 | 12/1995 | European Pat. Off. . |
| 0 702 228 A2 | 3/1996 | European Pat. Off. . |
| 08050112 A2 | 2/1996 | Japan . |
| WO 96/06347 | 2/1996 | WIPO . |

OTHER PUBLICATIONS

Caplus abstract of Peng et al. ("Determination of the neurotransmitter in the brain using composite polymer microelectrodes", Gaodeng Xuexiao Huaxue xuebao (1995), 16(12), 1847–51).

Caplus abstract of Zhang et al. ("Elimination of of the Acetaminophen Interference in the Implatable Glucose Sensor", Anal. Chem. (1994), 66(7), 1183–8).

Caplus abstract of JP 08050112 A2 (Masao Goto), Feb. 1996.

*Primary Examiner*—Robert J. Warden, Sr.
*Assistant Examiner*—Alex Noguerola
*Attorney, Agent, or Firm*—Akin, Gump, Strauss, Hauer & Feld, L.L.P.

[57] ABSTRACT

Disclosed is a biosensor facilitating high accuracy quantification of a specific component in a sample solution with no adverse influence of solid substances. The biosensor comprises an electrically insulating base plate, an electrode system comprising a working electrode and a counter electrode formed on the base plate, a reaction layer containing at least one enzyme disposed on the electrode system, and an anionic filter formed on the reaction layer for inhibiting permeation of solid components.

11 Claims, 2 Drawing Sheets

BIOSENSOR AND METHOD OF MANUFACTURING THE SAME

BACKGROUND OF THE INVENTION

The present invention relates to a biosensor for rapid and high accuracy quantification of a specific component contained in a sample and a method of manufacturing the same.

Conventionally, there is a disclosure of a biosensor as mentioned below as the system for facilitating simplified quantification of a specific component contained in a sample without necessitating dilution or agitation of the sample solution (Japanese Laid-Open Patent Publication Hei 3-202764).

More specifically, the biosensor is manufactured by forming an electrode system comprising a working electrode and a counter electrode on an electrically insulating base plate by screen printing and the like, and subsequently forming thereon an enzyme reaction layer comprising a hydrophilic polymer, an oxidoreductase, and an electron acceptor.

If a sample solution containing a substrate is dropped on the enzyme reaction layer of the biosensor thus produced, the enzyme reaction layer is dissolved, causing reaction between the substrate and the enzyme. As a result, the substrate is oxidized and, at the same time, the electron acceptor is reduced. Upon completion of the substrate-enzyme reaction, the reduced electron acceptor is electrochemically oxidized. The concentration of the substrate in the sample solution is then determined from the current value across the electrodes during this oxidation reaction.

The biosensor having the above-mentioned structure, however, has a drawback that even if the concentration of the substrate in the sample solution is equal, there arises a difference in the measured oxidation current value depending on other components contained in the sample solution.

One possible cause is interaction between solid substances exceeding 1 $\mu$m in size, such as hemocyte contained in the sample solution, and the electron acceptor reduced upon enzyme-substrate reaction. Close contact of the solid substances with the reduced electron acceptor will cause oxidation of the electron acceptor by the interaction therebetween, which leads to inaccurate measurement of the oxidation current value.

One effective measure for correcting this issue is to dilute the sample solution with a certain dilute solution in order to minimize the difference in the nature of the components contained in the sample solution. This method, however, is not necessarily advisable from the aspect of operability or controllability.

BRIEF SUMMARY OF THE INVENTION

The object of the present invention is to provide a biosensor which can overcome the above-mentioned problems.

The present invention provides a biosensor comprising an electrically insulating base plate, an electrode system having a working electrode and a counter electrode formed on the base plate, a reaction layer containing at least an enzyme disposed on the electrode system, and an anionic filter formed over the reaction layer for the purpose of inhibiting permeation of solid components.

In a preferred mode of the present invention, the anionic filter is composed of a porous film made of a film-forming polymer or a fiber sheet made by a paper machine, and an anionic polymer supported on the porous film or fiber sheet.

In another preferred mode of the present invention, the anionic filter is a porous film made of a mixture of a film-forming polymer and an anionic polymer.

According to the present invention, it is possible to provide a biosensor which facilitates high accuracy quantification of a substrate in a sample solution with no adverse effects of solid components coexisting with the substrate.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
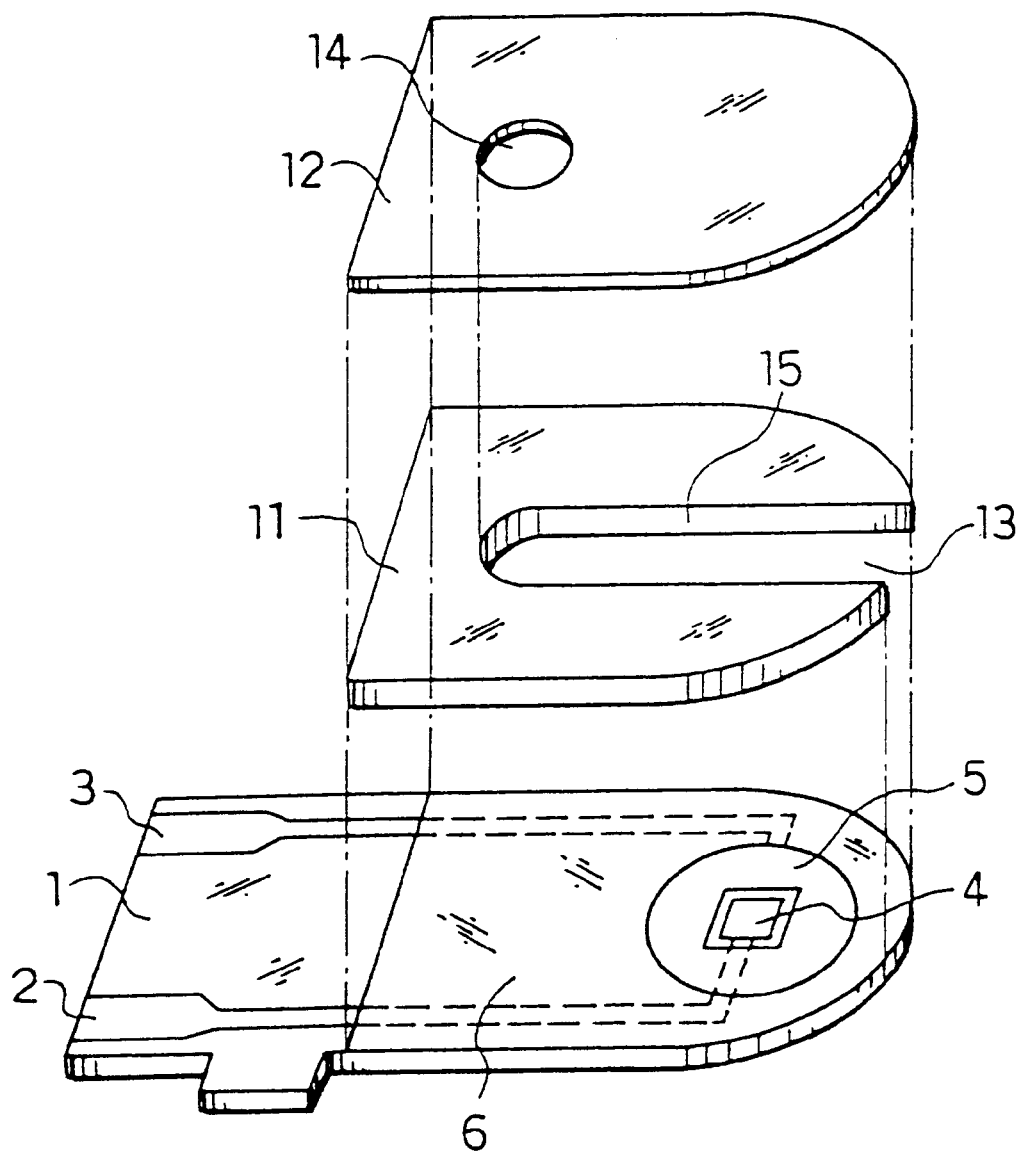
FIG. 1 shows a broken oblique perspective view of a biosensor in one example of the present invention, with omission of a reaction layer.

The anionic filter in accordance with the present invention may be composed of a combination of a filter for restricting movements of solid components in a sample solution and an anionic polymer for inhibiting dispersion of the electron acceptor contained in the reaction layer into the sample solution.

As the movement restricting filter, a porous film formed from a film-forming polymer or a glass fiber sheet made by a paper machine, a cellulose fiber or a resin fiber is preferable.

The preferable method for imparting an anionic property to the filter is to support an anionic polymer on the porous film or fiber sheet. It is also preferred to form the porous film from a mixture of a film-forming polymer and an anionic polymer.

As the measure for imparting the filter with the anionic property to obtain an anionic filter, it is preferable to contain the anionic polymer by not less than 5 wt % of the filter.

If the polymer used has the anionic as well as film-forming properties at the same time, then an anionic filter can be formed by using only this polymer.

The anionic filter in accordance with the present invention has two different functions as follows.

First, the smaller pore size of the anionic filter than the solid components in the sample solution prevents infiltration of solid components into the reaction layer.

Second, electrostatic repulsion of the anionic polymer contained in the anionic filter for the electron acceptor (which is an anionic compound) contained in the reaction layer inhibits dispersion of the electron acceptor in the sample solution beyond the filter.

The anionic filter separates the electron acceptor in the reaction layer from the solid components in the sample solution by the above-noted two functions. As a result, oxidation of the election acceptor which has been reduced upon enzyme-substrate reaction by the solid components in the sample solution can be prevented, and the adverse effect of the solid components on the sensor response can be minimized.

In order to express the first function, the anionic filter preferably has a pore size of not more than 1 $\mu$m to avoid permeation of solid components, such as hemocyte, for example, which are contained in the sample solution and will cause adverse effects on the sensor response.

As the film-forming polymer for constituting the anionic filter, at least one selected from the group consisting of ethyl cellulose, methyl cellulose, hydroxypropyl cellulose, cellulose acetate, nitrocellulose, polyvinyl pyrrolidone, polysulfon, polyvinylidene fluoride, polyamide and polyimide is preferably used.

As the anionic polymer which is another constituent for the anionic filter, at least one selected from the group consisting of polymers having at the side chain thereof a sulfonyl group, a sulfonic acid group or a carboxyl group is preferably used. The polymers may be exemplified as perfluorosulfonate ionomer, perfluorocarboxylate ionomer, polyacrylic acid, polymethacrylic acid, polyvinyl sulfate, polystyrene sulfonate, polyglutamic acid, polyaspartic acid, and carboxymethylcellulose.

The method of manufacturing a biosensor in accordance with the present invention comprises the steps dropping a solution containing a hydrophilic polymer over an electrode system disposed on an electrically insulating base plate and drying the solution to form a hydrophilic polymer layer on the electrode system, dropping a solution containing at least one enzyme on the hydrophilic polymer layer and drying the solution to form a reaction layer on the hydrophilic polymer layer, and forming an anionic filter for covering the reaction layer.

If the solution containing the enzyme is not agitated after dropping it on the hydrophilic polymer layer in the step of forming the reaction layer, the hydrophilic polymer layer would not be mixed with the enzyme layer, so that the surface of the electrode system can be covered with only the hydrophilic polymer layer. This prevents easy development of adverse changes in the performance of the electrode system due to adsorption of proteins onto the surface of the electrode system or chemical reaction caused by an oxidizing substance, such as electron acceptor which is sometimes contained in the reaction layer. Furthermore, since this structure increases dissolution of the reaction layer, a sensor response with high accuracy can be obtained.

The aforementioned anionic filter is formed by the four methods as exemplified below.

1. To form the anionic filter by the steps of disposing a medium dissolved or dispersed therein with a film-forming polymer on the reaction layer and drying the solution to form a filter, impregnating the filter formed from the film-forming polymer with a medium dissolved or dispersed therein with an anionic polymer to allow sufficient infiltration of the medium into the filter, and then drying the filter to obtain an anionic filter imparted with the anionic property.

At that time, it is preferable to select a medium which would not dissolve the filter formed from the film-forming polymer as the medium used for dissolving or dispersing the anionic polymer.

2. To form the anionic filter by the step of disposing a medium dissolved or dispersed therein with a film-forming polymer and an anionic polymer on the reaction layer and drying the medium.

3. To form the anionic filter by the steps of cutting a fiber sheet to a size which is large enough to cover the entire surface of the reaction layer and adhering it with pressure onto the reaction layer, impregnating the filter with a medium dissolved or dispersed therein with an anionic polymer to allow sufficient infiltration of the medium into the filter, and then drying the filter to obtain an anionic filter imparted with the anionic property.

4. To form the anionic filter by the steps of forming an anionic filter previously, then cutting the anionic filter to a size which is large enough to cover the entire surface of the reaction layer, and adhering it with pressure onto the reaction layer. As the anionic filter used here, one formed in advance on a base or the like different from the electrically insulating base plate by either method from 1 to 3 may be used. This method is useful if the medium in which at least one of the film-forming polymer and the anionic polymer is dissolved or dispersed is such a medium that could dissolve the reaction layer.

The step of disposing various mediums on the reaction layer, or impregnating the filter with those mediums is preferably performed by dropping, or immersion.

As the solvent for dissolving the anionic polymer, one selected from the group consisting of water, methanol, ethanol, propanol, butanol, acetone, toluene, xylene and ethyl ether, or a mixture of two or more of them is used preferably. The preferable choice is a solvent which would not dissolve the filter or the reaction layer formed.

As the enzyme contained in the reaction layer, either of glucose oxidase, glucose dehydrogenase, lactate oxidase, lactate dehydrogenase, fructose dehydrogenase, galactose oxidase, cholesterol oxidase, cholesterol dehydrogenase, cholesterol esterase, alcohol dehydrogenase, alcohol oxidase, ascorbate oxidase, bilirubin oxidase, or the like may be selected, depending on the measuring substrate of target.

Accordingly, the biosensor in accordance with the present invention is of wide applicability as a biosensor, such as glucose sensor, alcohol sensor, sucrose sensor, cholesterol sensor, lactose sensor, fructose sensor, and the like, which use an enzyme-associated reaction system.

As the electron acceptor, at least one selected from potassium ferricyanide, p-benzoquinone, phenazine methosulfate, indophenol and derivatives thereof, β-naphthoquinone-4-potassium sulfonate, methylene blue, and ferrocene and derivatives thereof is used.

As the hydrophilic polymer, at least one selected from carboxymethylcellulose, hydroxyethyl cellulose, hydroxypropyl cellulose, carboxyethylmethyl cellulose, polyvinyl pyrrolidone, polyvinyl alcohol, gelatin and derivatives thereof, polyacrylic acid, polyacrylates, polymethacrylic acid, polymethacrylates, starch and derivatives thereof, and polymers containing maleic anhydride or its salts is used.

As the solvent for dissolving the enzyme, the electron acceptor and the hydrophilic polymer, water or various buffer solutions including phosphate buffer solution, citrate buffer solution, acetate buffer solution, tris-hydrochloride buffer solution and the like may be used.

There are two methods for reacting the enzyme with the substrate: 1) by dissolving the reaction layer containing an enzyme in a sample solution containing a substrate to cause reaction between the enzyme and the substrate, and 2) by solidifying the reaction layer to prevent it from floating on the sample solution, thereby causing reaction between the enzyme and the substrate just upon the surface of the reaction layer.

The anionic filter in accordance with the present invention is also effective for such a biosensor that utilizes oxygen present in the sample solution as the electron acceptor due to the type of electrodes included.

The method of measurement of oxidation current includes two-electrode system comprising a measuring electrode and a counter electrode and three-electrode system further comprising a reference electrode; the latter permits more accurate measurement.

In the following, the present invention will be described more specifically by way of concrete examples. FIG. 1 is a broken oblique perspective view of a biosensor with omission of a reaction layer. A biosensor is assembled by joining an electrically insulating base plate 1 disposed with an electrode system, cover 12 provided with an air vent 14 and a spacer 11 in a positional relationship as shown by the dotted line in FIG. 1.

In the biosensor thus obtained, since a cavity for constituting a sample solution supply pathway is formed in a slit 15 of the spacer 11 between the base plate 1 and the cover 12, a sample solution can be introduced into the reaction layer readily through the sample solution supply pathway by simply contacting the sample solution with a tip 13 of the slit 15 serving as an opening. With this structure, the supply amount of the sample solution depends on the volume of the cavity formed by the cover 12 and the spacer 11, so that pre-quantification of the sample solution is unnecessary. In addition, this structure minimizes evaporation of the sample solution during measurement, facilitating high accuracy measurement. The use of a transparent polymer material for the cover and the spacer permits easy observation of the conditions of the reaction layer and introduction of the sample solution from the outside.

Figure 2:
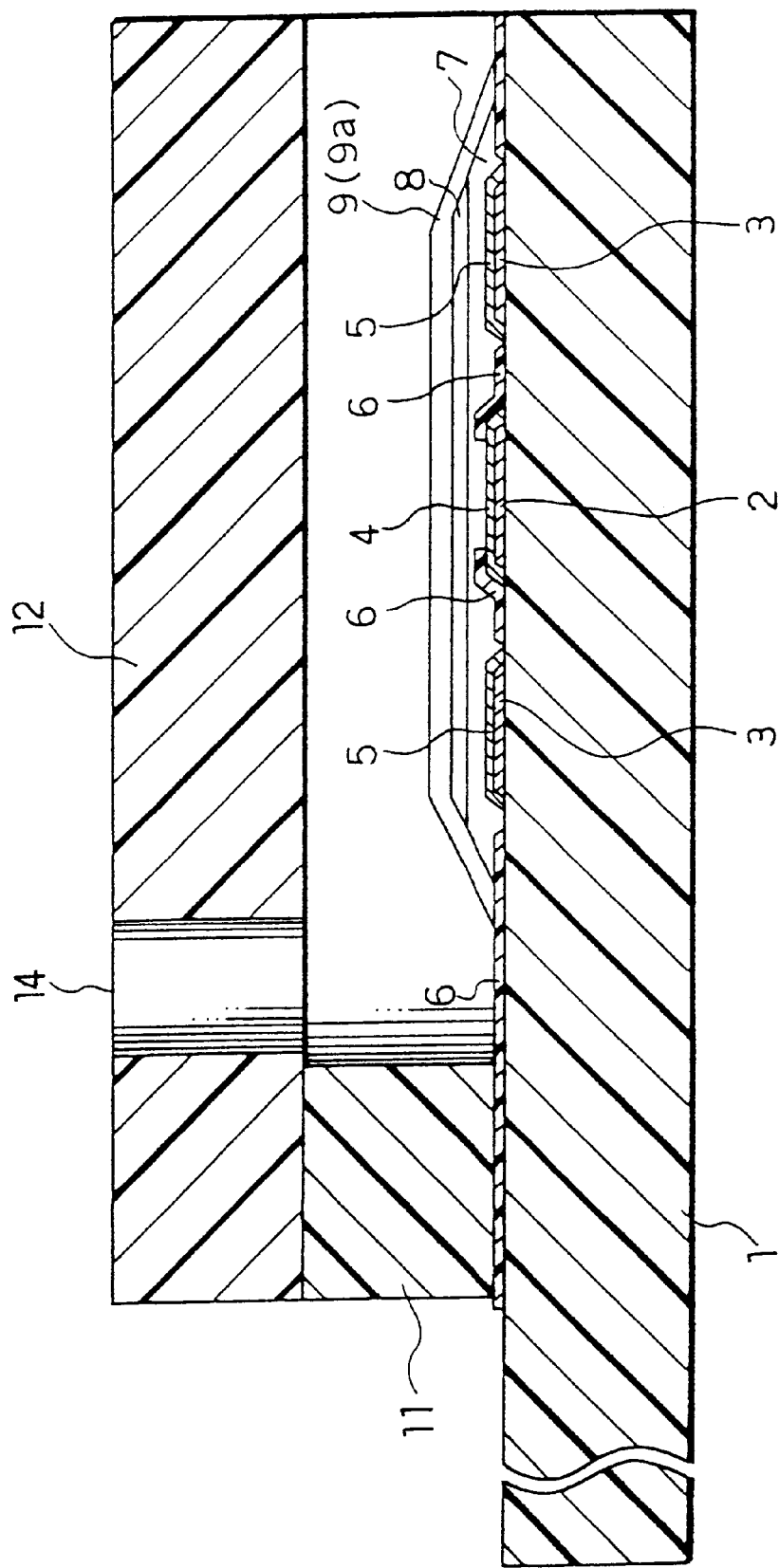
FIG. 2 shows a longitudinal cross-sectional view illustrating the vital parts of the biosensor.

FIG. 2 shows a longitudinal cross-sectional view of the biosensor in accordance with the present invention.

First, the electrically insulting base plate 1 is provided with leads 2 and 3 by screen-printing a silver paste thereon. The base plate 1 is further disposed thereon with an electrode system comprising a working electrode 4 and a counter electrode 5 each made of a conductive carbon paste containing a resin binder, and an electrically insulating layer 6 made of an electrically insulating paste. The layer 6 has two functions to hold the areas where the working electrode 4 and the counter electrode 5 are exposed constant, and to cover part of the leads. Then, a hydrophilic polymer layer 7 is formed on the electrode system. Subsequently, an enzyme layer 8 is formed on the hydrophilic polymer layer 7. The two layers thus formed are then covered with an anionic filter 9 or a filter 9a. The enzyme layer 8 further contains an electron acceptor depending on the material used for the electrode system.

EXAMPLE 1

First, a 0.5 wt % aqueous solution of sodium salt of carboxymethylcellulose (hereinafter abbreviated to "CMC") was dropped over the electrode system disposed on the electrically insulating base plate 1 as shown in FIG. 2 and dried at 50° C. for 10 minutes in a hot drier to form the hydrophilic polymer layer 7 (CMC layer). Subsequently, a mixture aqueous solution containing glucose oxidase (EC1.1.3.4; hereinafter abbreviated to "GOD") at 10 mg/ml and potassium ferricyanide at 16 mg/ml was prepared. The mixture aqueous solution thus prepared was dropped over the CMC layer 7 and dried at 50° C. for another 10 minutes in a hot drier to form the enzyme layer Then, a mixture ethanol solution A was formulated by mixing a 2 wt % ethanol solution of ethyl cellulose and a 0.5 wt % ethanol solution of hydroxypropyl cellulose. An aliquot of 5 $\mu$l of the mixture ethanol solution A was dropped on the enzyme layer 8 and dried for 10 minutes at room temperature to form a filter comprising a film-forming polymer. Then, for imparting the filter thus formed with an anionic property, an aliquot of 5 $\mu$l of a 1 wt % butanol solution of perfluorosulfonate ionomer was dropped on the filter and dried at 50° C. for 10 minutes. This gave the anionic filter 9.

Finally, the cover 12 and the spacer 11 were adhered to the base plate 1 in the positional relationship as shown by the dotted line in FIG. 1. In this way, a glucose sensor of this example was produced.

Separately, a blood sample solution and a glucose aqueous solution for this glucose sensor were prepared by adjusting the concentration of glucose in each solution equal. An aliquot of 3 $\mu$l of each sample solution was supplied from the opening 13 of the sample solution supply pathway.

After introduction through the opening 13, the sample solution reaches the air vent 14 and infiltrates the anionic filter 9. The solution which has passed through the anionic filter causes dissolution of the reaction layer. In the reaction layer, the glucose contained in the sample solution is oxidized by the glucose oxidase present in the reaction layer, which causes electron movement, and the electron moved reduces potassium ferricyanide to potassium ferrocyanide.

One minute after introduction of the sample solution, a voltage of +0.5 V on the basis of the voltage of the counter electrode 5 was applied to the working electrode 4 and the anodic current value was measured after 5 seconds. The measurement results showed that the current value in response to the blood sample solution was about 98% of that in response to the glucose aqueous solution.

EXAMPLE 2

In this example, the hydrophilic polymer layer 7 and the enzyme layer 8 were formed over the electrode system disposed on the electrically insulating base plate 1 as shown in FIG. 2 in the same manner as in Example 1.

Then, an aliquot of 5 $\mu$l of the mixture ethanol solution A, which was prepared in Example 1, was dropped on the enzyme layer 8 and dried for 10 minutes at room temperature to form a filter comprising a film-forming polymer. Subsequently, for imparting the anionic property to this filter, an aliquot of 5 $\mu$l of a 1 wt % aqueous solution of polyacrylic acid was dropped on the filter and dried at 50° C. for 10 minutes. This gave the anionic filter 9.

Finally, a glucose sensor of this example was produced in the same manner as in Example 1, and the sensor responses to the glucose aqueous solution and the blood sample solution were measured. The measurement results showed that the current value in response to the blood sample solution was about 95% of that in response to the glucose aqueous solution.

EXAMPLE 3

In this example, the hydrophilic polymer layer 7 and the enzyme layer 8 were formed over the electrode system disposed on the electrically insulating base plate 1 as shown in FIG. 2 in the same manner as in Example 1.

Then, a mixture ethanol solution B was formulated by mixing a 2 wt % ethanol solution of ethyl cellulose and a 0.2 wt % ethanol solution of perfluorocarboxylate ionomer. An aliquot of 5 $\mu$l of the mixture ethanol solution B was dropped on the enzyme layer 8 and dried for 10 minutes at room temperature to form the anionic filter 9.

Finally, a glucose sensor of this example was produced in the same manner as in Example 1, and the sensor responses to the glucose aqueous solution and the blood sample solution were measured. The measurement results showed that the current value in response to the blood sample solution was about 97% of that in response to the glucose aqueous solution.

EXAMPLE 4

In this example, the hydrophilic polymer layer 7 and the enzyme layer 8 were formed over the electrode system disposed on the electrically insulating base plate 1 as shown in FIG. 2 in the same manner as in Example 1.

Then, a glass fiber sheet was cut to a size which is large enough to cover the entire surface of the reaction layer and adhered with pressure to the reaction layer to form a filter. Subsequently, an aliquot of 10 μl of a 0.5 wt % ethanol solution of perfluorosulfonate ionomer was dropped on the filter and dried for 10 minutes at room temperature. In this way, the filter was imparted with the anionic property and the anionic filter 9 was obtained.

Finally, a glucose sensor of this example was produced in the same manner as in Example 1, and the sensor responses to the glucose aqueous solution and the blood sample solution were measured. The measurement results showed that the current value in response to the blood sample solution was about 98% of that in response to the glucose aqueous solution.

EXAMPLE 5

In this example, the hydrophilic polymer layer 7 and the enzyme layer 8 were formed over the electrode system disposed on the electrically insulating base plate 1 as shown in FIG. 2 in the same manner as in Example 1.

Then, the anionic filter 9 was formed in the same manner as in Example 4, except for the use of a cellulose fiber sheet in place of the glass fiber sheet.

Finally, a glucose sensor of this example was produced in the same manner as in Example 1, and the sensor responses to the glucose aqueous solution and the blood sample solution were measured. The measurement results showed that the current value in response to the blood sample solution was about 95% of that in response to the glucose aqueous solution.

EXAMPLE 6

In this example, the hydrophilic polymer layer 7 and the enzyme layer 8 were formed over the electrode system disposed on the electrically insulating base plate 1 as shown in FIG. 2 in the same manner as in Example 1.

Then, a filter was formed in the same manner as in Example 4 by adhering with pressure a cellulose fiber sheet to the reaction layer. Subsequently, a 1% aqueous solution of polyacrylic acid was formulated and an aliquot of 10 μl of the solution was dropped on the filter and dried at 50° C. for 10 minutes, which gave the anionic filter 9.

Finally, a glucose sensor of this example was produced in the same manner as in Example 1, and the sensor responses to the glucose aqueous solution and the blood sample solution were measured. The measurement results showed that the current value in response to the blood sample solution was about 97% of that in response to the glucose aqueous solution.

EXAMPLE 7

In this example, the hydrophilic polymer layer 7 and the enzyme layer 8 were formed over the electrode system disposed on the electrically insulating base plate 1 as shown in FIG. 2 in the same manner as in Example 1.

Then, an aliquot of 5 μl of the mixture ethanol solution B, which was prepared in Example 3, was dropped on a glass plate and dried for 10 minutes at room temperature to form the anionic filter 9 composed of a mixture of a film-forming polymer and an anionic polymer. Subsequently, the filter thus formed was peeled off from the glass plate, then cut to a size which is large enough to cover the entire surface of the enzyme layer 8, and adhered with pressure to the enzyme layer 8.

Finally, a glucose sensor of this example was produced in the same manner as in Example 1, and the sensor responses to the glucose aqueous solution and the blood sample solution were measured. The measurement results showed that the current value in response to the blood sample solution was about 95% of that in response to the glucose aqueous solution.

EXAMPLE 8

In this example, the hydrophilic polymer layer 7 and the enzyme layer 8 were formed over the electrode system disposed on the electrically insulating base plate 1 as shown in FIG. 2 in the same manner as in Example 1.

Then, a glass fiber filter was immersed in a 2% ethanol solution of perfluorosulfonate ionomer, and then dried at room temperature for 10 minutes, followed by further drying at 50° C. for another 5 minutes in a hot drier. In this way, the glass fiber filter was imparted with the anionic property and an anionic filter was obtained. Subsequently, the anionic filter thus formed was cut to a size which is large enough to cover the entire surface of the reaction layer, and adhered with pressure to the reaction layer.

Finally, a glucose sensor of this example was produced in the same manner as in Example 1, and the sensor responses to the glucose aqueous solution and the blood sample solution were measured. The measurement results showed that the current value in response to the blood sample solution was about 95% of that in response to the glucose aqueous solution.

Comparative Example 1

For comparison, the hydrophilic polymer layer 7 and the enzyme layer 8 were formed over the electrode system disposed on the electrically insulating base plate 1 as shown in FIG. 2 in the same manner as in Example 1, except for omission of the anionic filter 9.

Then, a glucose sensor of this comparative example was produced in the same manner as in Example 1, and the sensor responses to the glucose aqueous solution and the blood sample solution were measured. The measurement results showed that the current value in response to the blood sample solution was about 70 to 80% of that in response to the glucose aqueous solution.

Comparative Example 2

For comparison, the hydrophilic polymer layer 7 and the enzyme layer 8 were formed over the electrode system disposed on the electrically insulating base plate 1 as shown in FIG. 2 in the same manner as in Example 1.

Then, an aliquot of 5 μl of a 2 wt % ethanol solution of ethyl cellulose was dropped on the enzyme layer 8 and dried for 10 minutes at room temperature to form the filter 9a. The filter 9a comprising a film-forming polymer was not imparted with the anionic property.

Finally, a glucose sensor of this comparative example was produced in the same manner as in Example 1, and the sensor responses to the glucose aqueous solution and the blood sample solution were measured. The measurement results showed that the current value in response to the blood sample solution was about 83% of that in response to the glucose aqueous solution.

Comparative Example 3

For comparison, the hydrophilic polymer layer 7 and the enzyme layer 8 were formed over the electrode system disposed on the electrically insulating base plate 1 as shown in FIG. 2 in the same manner as in Example 1.

Then, an aliquot of 5 μl of a 0.1 wt % ethanol solution of perfluorosulfonate ionomer was dropped on the enzyme layer 8 and dried for 10 minutes at room temperature. In this way, an anionic polymer was adhered to the enzyme layer 8.

Finally, a glucose sensor of this comparative example was produced in the same manner as in Example 1, and the sensor responses to the glucose aqueous solution and the blood sample solution were measured. The measurement results showed that the current value in response to the blood sample solution was about 73% of that in response to the glucose aqueous solution.

Comparative Example 4

For comparison, the hydrophilic polymer layer 7 and the enzyme layer 8 were formed over the electrode system disposed on the electrically insulating base plate 1 as shown in FIG. 2 in the same manner as in Example 1.

Then, a glass fiber sheet was adhered to the reaction layer with pressure in the same manner as in Example 4 to form the filter 9a on the reaction layer. The filter 9a was not imparted with the anionic property.

Finally, a glucose sensor of this comparative example was produced in the same manner as in Example 1, and the sensor responses to the glucose aqueous solution and the blood sample solution were measured. The measurement results showed that the current value in response to the blood sample solution was about 80% of that in response to the glucose aqueous solution.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A biosensor comprising an electrically insulating base plate, an electrode system having a working electrode and a counter electrode formed over said base plate, a water soluble reaction layer containing at least an enzyme and an electron acceptor disposed on said electrode system, and an anionic filter formed over said reaction layer for inhibiting permeation of solid components, wherein said anionic filter is composed of a porous film made of a film-forming polymer or a fiber sheet, and an anionic polymer for inhibiting by electrostatic repulsion dispersion of said electron acceptor beyond said anionic filter, wherein said anionic polymer is supported on said porous film or fiber sheet.

2. The biosensor in accordance with claim 1, wherein said film-forming polymer is at least one selected from the group consisting of ethyl cellulose, methyl cellulose, hydroxypropyl cellulose, cellulose acetate, nitrocellulose, polyvinyl pyrrolidone, polysulfon, polyvinylidene fluoride, polyamide and polyimide, and said anionic polymer is at least one selected from the group consisting of polymers having at the side chain thereof at least one functional group selected from the group consisting of a sulfonyl group, a sulfonate group and a carboxyl group.

3. A biosensor comprising an electrically insulating base plate, an electrode system having a working electrode and a counter electrode formed over said base plate, a water soluble reaction layer containing at least an enzyme and an electron acceptor disposed on said electrode system, and an anionic filter formed over said reaction layer for inhibiting permeation of solid components, wherein said anionic filter is a porous film made of a mixture of a film-forming polymer and an anionic polymer for inhibiting by electrostatic repulsion dispersion of said electron acceptor beyond said anionic filter.

4. The biosensor in accordance with claim 3, wherein said film-forming polymer is at least one selected from the group consisting of ethyl cellulose, methyl cellulose, hydroxypropyl cellulose, cellulose acetate, nitrocellulose, polyvinyl pyrrolidone, polysulfone, polyvinylidene fluoride, polyamide and polyimide, and said anionic polymer is at least one selected from the group consisting of polymers having at the side chain thereof at least one functional group selected from the group consisting of a sulfonyl group, a sulfonate group and a carboxyl group.

5. A method of manufacturing a biosensor comprising the steps of:

dropping a solution containing a hydrophilic polymer on an electrode system disposed on an electrically insulating base plate and drying said solution to form a hydrophilic polymer layer on said electrode system, dropping a solution containing at least one enzyme and an electron acceptor on said hydrophilic polymer layer and drying the solution to form a water soluble reaction layer on said hydrophilic polymer layer, and forming an anionic filter for covering said reaction layer said anionic filter inhibiting by electrostatic repulsion dispersion of said electron acceptor beyond said anionic filter.

6. The method of manufacturing a biosensor in accordance with claim 5, wherein the step of forming said anionic filter comprises the step of disposing a medium, having a film-forming polymer and an anionic polymer dissolved or dispersed therein, on said reaction layer and drying the medium to form an anionic filter.

7. The method of manufacturing a biosensor in accordance with claim 5, wherein the step of forming said anionic filter comprises the steps of:

adhering with pressure a fiber sheet onto said reaction layer to form a filter, and impregnating said filter with a medium, having an anionic polymer dissolved or dispersed therein, and drying the filter to obtain an anionic filter imparted with an anionic property.

8. The method of manufacturing a biosensor in accordance with claim 5, wherein the step of forming said anionic filter comprises the step of adhering with pressure a prefabricated anionic filter onto said reaction layer.

9. The method of manufacturing a biosensor in accordance with claim 5, wherein the step of forming said anionic filter comprises the steps of:

disposing a medium, having a film-forming polymer dissolved or dispersed therein, on said reaction layer and drying the medium to form a filter, and impregnating said filter with a medium, having an anionic polymer dissolved or dispersed therein, and drying the filter to form an anionic filter imparted with an anionic property.

10. The method of manufacturing a biosensor in accordance with claim 9, wherein said medium for dissolving or dispersing said anionic polymer is one that would not dissolve said film-forming polymer.

11. A method of manufacturing a biosensor comprising the steps of: forming a water soluble reaction layer including an enzyme, an electron acceptor and a hydrophilic polymer on an electrode system having a working electrode and a counter electrode disposed on an electrically insulating base plate, and disposing a medium, having a film-forming polymer and an anionic polymer dissolved or dispersed therein, on said reaction layer and drying the medium to form an anionic filter wherein said anionic polymer inhibits by electrostatic repulsion dispersion of said electron acceptor beyond said anionic filter.

* * * * *